United States Patent [19]

Date et al.

[11] Patent Number: 4,733,963

[45] Date of Patent: Mar. 29, 1988

[54] METHOD OF MEASURING A SOUND PRESSURE DISTRIBUTION IN A SOLID BODY DUE TO A ULTRASONIC PROBE BY USING PHOTOELASTICITY

[75] Inventors: Kazuhiro Date; Heihachi Shimada, both of Sendai, Japan

[73] Assignee: Krautkramer Foerster Japan Co., Ltd., Japan

[21] Appl. No.: 928,818

[22] Filed: Nov. 7, 1986

[30] Foreign Application Priority Data

Nov. 9, 1985 [JP] Japan ................................ 60-251804

[51] Int. Cl.⁴ ........................ G01L 1/24; G01N 21/00
[52] U.S. Cl. ........................................ 356/35; 73/800; 356/33; 356/237
[58] Field of Search ............... 356/32, 33, 34, 35, 356/35.5, 237, 239; 250/225; 73/774, 778, 800, 801, 804

[56] References Cited

U.S. PATENT DOCUMENTS 3,763,698  10/1973  Suzuki et al. .................. 73/800 X

*Primary Examiner*—Eugene R. Laroche
*Assistant Examiner*—Robert J. Pascal
*Attorney, Agent, or Firm*—Ostrolenk, Faber, Gerb & Soffen

[57] ABSTRACT

A method for obtaining quantitative data which relates the sound pressure distribution in a body to an ultrasound pulse waveform which propagates through the body, based on photoelastic measurement and analysis. The method involves producing a first image of the body, into which the ultrasound pulse was launched, by recording the image of linearly polarized straboscopic light which is directed into the body. Thereafter, a second image is taken of the stroboscopic light with the principal axis of the linear polarizer offset by 45° relative to the first image. The first and second images are combined to produce a synthesized image and the above-mentioned quantitative data is derived from the synthesized image.

9 Claims, 13 Drawing Figures

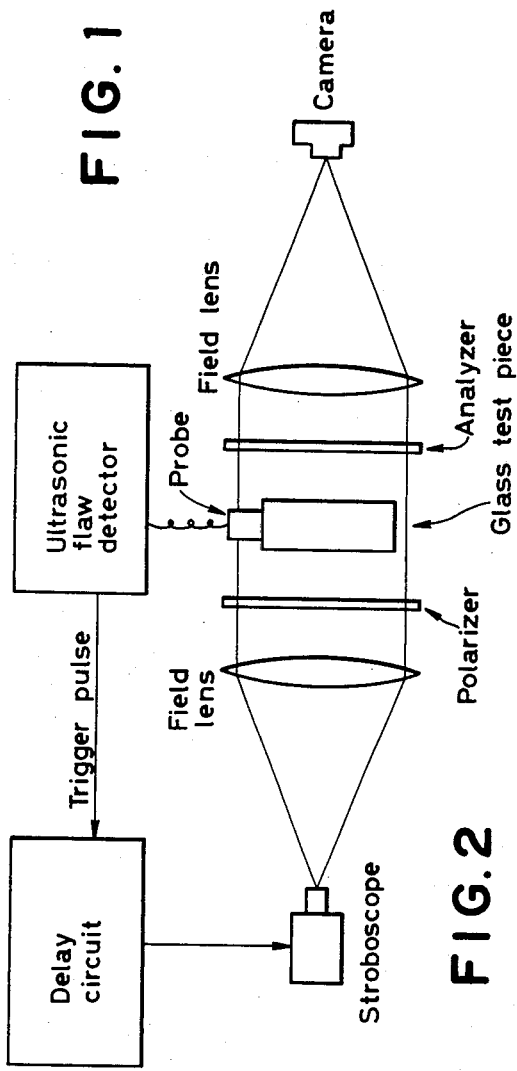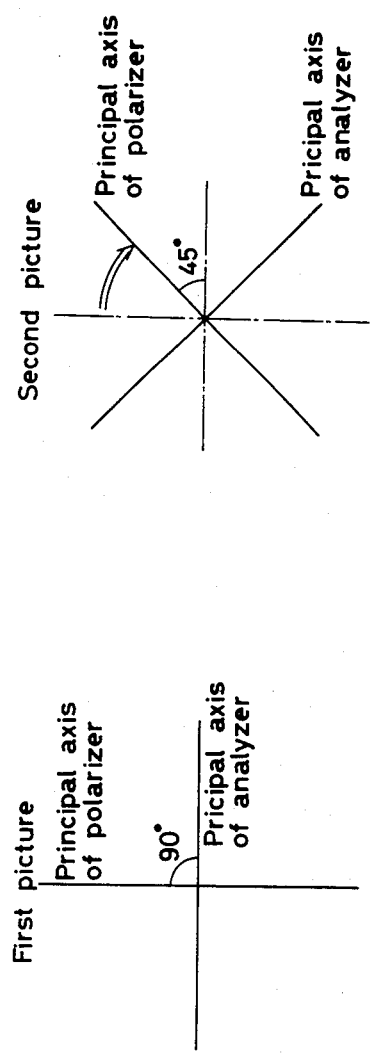

FIG.11
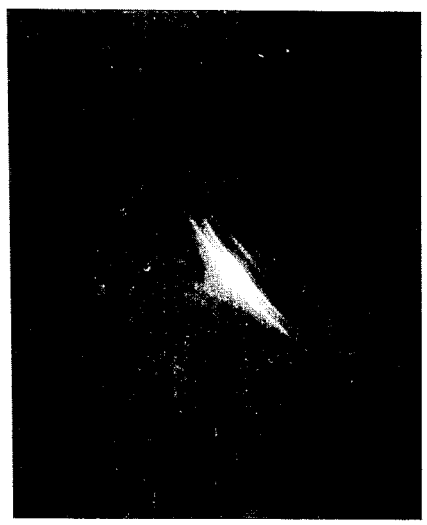
FIG.11A

METHOD OF MEASURING A SOUND PRESSURE DISTRIBUTION IN A SOLID BODY DUE TO A ULTRASONIC PROBE BY USING PHOTOELASTICITY

BACKGROUND OF THE INVENTION

1. Field of the Invention

The need exists for a reliable non-destructive test for detecting defects in material used for fabricating defect-free objects of high safety and reliability as are required for use in applications such as atomic power and stream power equipments, airplanes, automobiles, chemical plant and machines; iron frame structures in buildings and bridges; and ceramic members.

Ultrasonic flaw detection provides a non-destructive test for detecting defects in materials. An ultrasonic pulse (hereinafter referred to simply as pulse) is emitted from an ultrasonic probe (hereinafter referred to simply as probe) into the object. The pulse is reflected from a defect, if any, and such reflection is detected by the probe thereby to detect the fault in the material. The ultrasonic flaw detection is most generally used for objects of the type mentioned above.

The probe is generally of the ceramic type and it is configured as a piezoelectric transducer. Its characteristics deviate from probe to probe by reason of manufacturing tolerances, and further is frequently exchanged as consumption goods. It is necessary, however, to obtain consistent and reliable quantitative analysis characteristics and a uniformity in test results for similar defects regardless of the probe used. Also needed is an ability to determine a tolerance of the sound pressure distribution of the pulse emitted from each probe. Furthermore, to avoid detection of a fault in actual flaw detection, one must be able to select a suitable probe, an arrangement and a scanning pitch of the probe for the particular application. The most important factors for carrying out the ultrasound fault detection procedure require measurement and assessment of the. pulse waveform emitted from the probe, the sound pressure distribution relative to the waveform, and the changes in their propagation through the object.

The present invention provides a quantitative measuring method for measuring the pulse waveform and the sound pressure distribution on the waveform by emitting from the probe a pulse into a transparent solid model of the object which will be tested. By using photoelasticity, the method enables evaluation of the characteristics concerning the sound pressure distribution of the particular probe, by carrying out tests on a transparent solid model of the material to be tested. The transparent model material is selected to have characteristics which are similar to those of the actually to be tested material. The present invention allows various probes to be characterized and is effective to enable selection of probes suitable for most detecting particular defects, arrangement of probes, determination of a scanning pitch thereof, and a development of new probes. The method serves to improve the reliability and the precision available with ultrasonic flaw detection.

Furthermore, since an ultrasonic pulse produces a weak stress wave in the material, the method of the present invention relates to a technique for measuring weak stresses with sensitivities which are much higher than those available with conventional photoelastic stress measuring techniques. Therefore, the present method can be utilized for static weak stress measurements and for dynamic weak stress measurements of repeat phenomenon.

2. Description of the Prior Art

There are three kinds of methods for measuring pulse waveforms and sound pressure distributions of the pulse emitted from the probe. One of them calls for visually measuring and evaluating the pulse actually launched from the probe into a model material which is similar to the material to be used, in a manner similar to the photoelasticity and the Schilieren methods. Another method uses a standard test piece having minute reflectors in lateral and vertical holes using the actual material to be tested. The last method relies on receiving the pulse emitted from the probe by using an electro-dynamic sensor.

In the above-mentioned methods which use the standard test piece or the electro-dynamic sensor, the sound pressure distribution is consequently evaluated taking account of the characteristics of the probe for receiving the pulse and the electro-dynamic sensor. Therefore, only the relative sound pressure distribution can be measured and information concerning the absolute value of the pulse waveform and the sound pressure can not be obtained. Furthermore, there are disadvantages that the frequency characteristic of the reflection due to the minute reflection body in the standard test piece is very unique, and the reflection waveform is undesirably dependent on the input waveform.

It is assumed that it is effective that the method of visually evaluating the pulse has a possibility of measuring the pulse waveform and the sound pressure on the waveform. However, since the Schilieren method does not provide a visual image which is proportional to the sound pressure, obtaining a quantitative measurement is difficult. In contrast, according to the photoelastic method a principal stress difference can be measured. Therefore, the sound pressure of the ultrasonic pulse can be measured directly.

The conventional photoelastic method for visually measuring the pulse uses two kinds of approaches. One relies on a linear polariscope and the other on a circular polariscope, in which a stroboscopic light source having a short flash time is used for obtaining a still picture of the pulse travelling with high speed. In the method using the linear polariscope, a high sensitivity sufficient for obtaining a visual image of the pulse can be obtained, but the visual image is undesirably changed in accordance with the direction of the incident polarized light used, because of the linear polarization, therefore a quantitative measurement can not be obtained. On the other hand, in the case of the method using the circular polariscope, a visual image proportional to a principal stress difference can be obtained in principle. Therefore, the quantitative measurement of the pulse waveform and the sound pressure distribution can be obtained. In this case, however, a detailed quantitative measurement can not be achieved because of low sensitivity in visualizing the pulse generated by the conventional ultrasonic flaw detecting apparatus and its probe. Therefore, development of a method for obtaining a visual image of the pulse with high sensitivity by using the photoelastic method has been expected.

OBJECT OF THE INVENTION

In the principle photoelastic method using the circular polariscope provides a visual image with which it is possible to measure the pulse waveform and the sound pressure distribution on the waveform of the pulse emitted from the probe. In practice, however, the method fails on account of low sensitivity.

It is an object of the present invention is to provide a photoelastic method which attains a sensitivity which is high enough to provide sound-pressure-distribution resolution which is comparable to that obtained from the photoelastic method using the circular polariscope. The method produces a visual image of the pulse generated by the combination of the conventional ultrasonic flaw detector and the probe, and enables measurement of the pulse waveform and the sound pressure distribution on the waveform from the visual image. It is then possible to evaluate and characterize the sound pressure characteristics of the probe.

BRIEF DESCRIPTION OF THE DRAWINGS

FIG. 1 is a block diagram of an apparatus for visualizing an ultrasonic pulse generated by the combination of the photoelastic apparatus of the linear polarization type and the stroboscopic light source.

FIG. 2 is provided for explaining the brightness at predetermined points when the same stress field is observed at the linearly polarized lights which are separated from each other on the principal axis by 45°.

FIGS. 10-13 are reference photographs.

FIGS. 10 and 11 are each two visual images obtained by the present invention.

FIGS. 12 and 13 are visual images obtained by the conventional method.

DETAILED DESCRIPTION OF THE INVENTION

Figure 3:
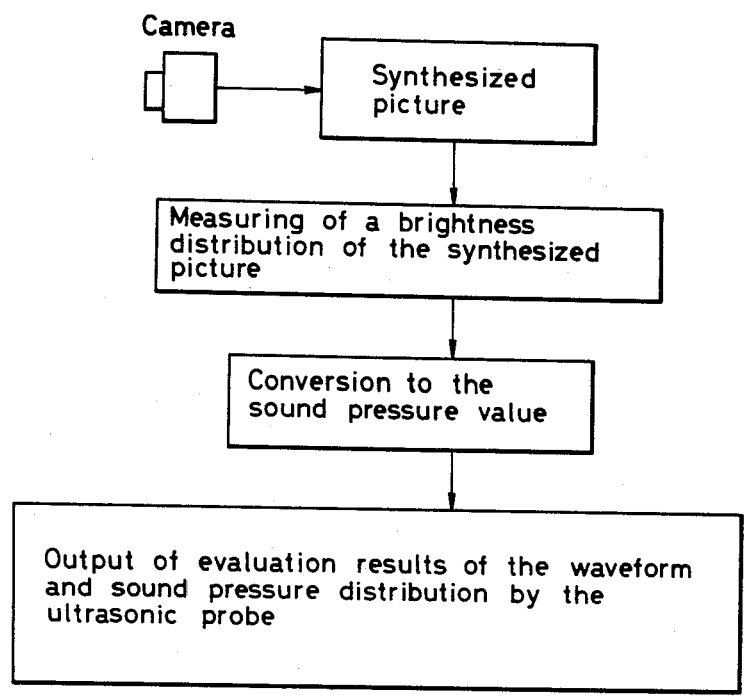
FIG. 3 is a flowchart showing the method of the present invention, from the step of synthesizing a picture to the step of sound pressure distribution measurement.

As mentioned in FIG. 1, the pulse generated by the conventional ultrasonic flaw detector is emitted from the conventional probe into a transparent test piece of glass, as is known from conventional flaw detection methods. On the other hand, a trigger pulse is fetched from the ultrasonic flaw detector in synchronism with the pulse emitted into the glass test piece to apply it to a delay circuit for providing a delay time and further to actuate a stroboscope. The reason for using glass is that the ultrasonic wave velocity of glass is similar to that of the steel material tested most frequently. If the photoelastic apparatus of the linearly polarized light type is combined with the test piece of glass, the pulse can be visually observed since the pulse in the glass test piece is a stress wave. Th visual image obtained by the apparatus shown in FIG. 1 is the conventional visual image of the linear polarization. A quantitative analysis can not therefore be obtained because of the linear polarization.

In FIG. 2 there are shown two pictures of linear polarization in which the principal axis of the polarizer is always perpendicular to the principal axis of the analyzer and each principal axis in the first picture is 45° different from each principal axis in the second picture. If polarized light passes through identical stress fields, the following equation is obtained for the first picture.

$$I_1 = a^2 \cdot \sin^2 2\theta \cdot \sin^2 \frac{\delta}{2} \qquad (1)$$

where, $I_1$ is brightness at predetermined points on the first picture; "a" is a constant; $\theta$ is the angle between the principal axis and the principal stress direction of the stress field; and $\delta$ represents the following equation;

$$\delta = C \cdot d \cdot (\sigma_1 - \sigma_2) \qquad (2)$$

where C is a photoelastic constant; d is the thickness of the test piece; and $\sigma_1$ and $\sigma_2$ represent principal stress.

On the other hand, for the second picture the following equation is obtained.

$$I_2 = a^2 \cdot \cos^2 2\theta \cdot \sin^2 \frac{\delta}{2} \qquad (3)$$

Where, $I_2$ is brightness at the predetermined points on the second picture; a, $\theta$ and $\delta$ are the same quantities as mentioned in equation (1); and especially $\theta$ is the value on the first picture.

In the case of the synthesized picture in which the brightness of the first picture is added to that of the second picture, the brightness at the predetermined points on the synthesized picture is represented as follows.

$$I = I_1 + I_2 = a^2 \cdot \sin^2 \frac{\delta}{2} \qquad (4)$$

Referring to the equation (2), the brightness at the predetermined points on the synthesized picture corresponds to only the principal stress difference, and the relationship between the brightness and the stress value is the same as the case of the circular polarization. The brightness corresponds to the principal stress difference as mentioned above, but since the relation between the principal stress components of longitudinal wave and shear wave are known in the case of ultrasonic pulse, the sound pressure can be measured and evaluated at the predetermined points by measuring the brightness of the synthesized picture by using the equation (4).

The flow of the measurement process is shown in FIG. 3.

There are shown examples for measuring the sound pressure distribution of an ultrasonic pulse generated from a normal longitudinal wave probe and a angle shear wave probe. The visual image obtained by the circular polariscope is also shown in FIGS. 10-13.

Such measurement is obtained by the apparatus shown in FIG. 1. The ultrasonic flaw detecting apparatus and the probe are commercially available. The frequency of the probe is 2 MHz. The probe has a diameter of 20 mm for the longitudinal wave and 22×22 mm for the shear wave. Pyrex glass having the dimension 100×100 mm of square and thickness of 20 mm was used for a glass test piece. The pyrex glass has a wave speed of 5490 m/sec for longitudinal waves and 3420 m/sec for shear waves which values are similar to those of steel. Having further a high sensitivity of photoelasticity, the pyrex glass sufficiently simulates actual test material for the ultrasonic flaw detection test. A stroboscope was used having a flash time of 150 ns.

Figure 10:
Figure 10A:
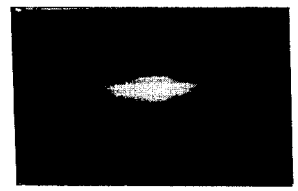
Figure 12:
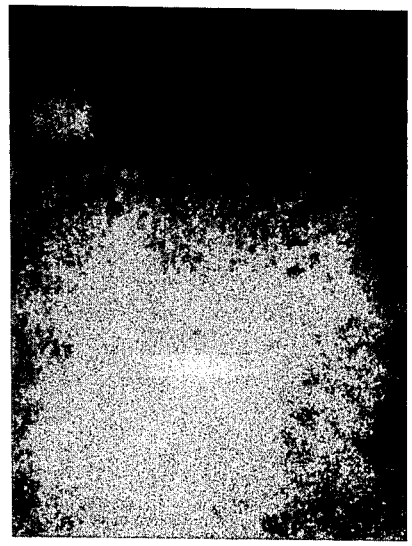
Figure 13:

Synthesization of pictures was effected by a conventional 35 mm camera. The first and the second pictures are double exposed on the same film frame. The longitudinal wave of the synthesized picture thus obtained is shown in FIG. 10 and the shear wave thereof is shown in FIG. 11. Since ordinary print paper has limited contrast showing characteristics, it is not possible to show the images of the film on a single print paper. Therefore two images having densities different from each other are used for the purpose of showing the required detail. As is apparent from the above, according to the method of the present invention the ultrasonic pulse can be visually observed very clearly. FIGS. 12 and 13 show photographs recorded with the same image by the circular polarization. As is apparent from FIGS. 12 and 13 in comparison with FIGS. 10 and 11 according to the visual image by the circular polarization, they are at most recognized as the pulse and it is not possible to achieve the quantitative evaluation.

Figure 4:
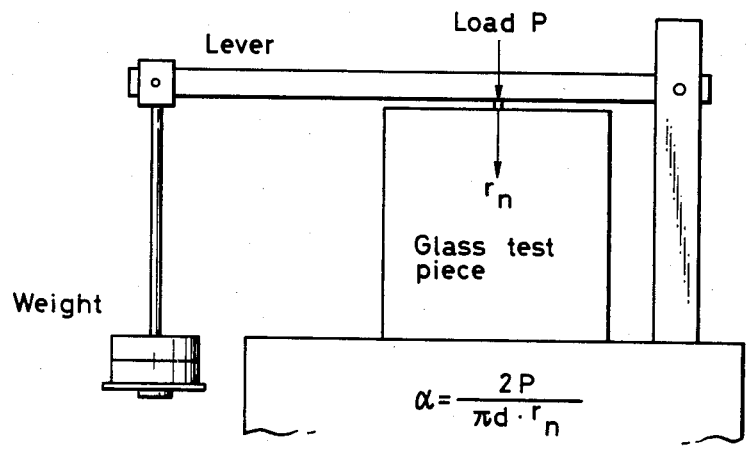
FIG. 4 is a front view of a calibrating apparatus for a sound pressure apparatus.
Figure 5:
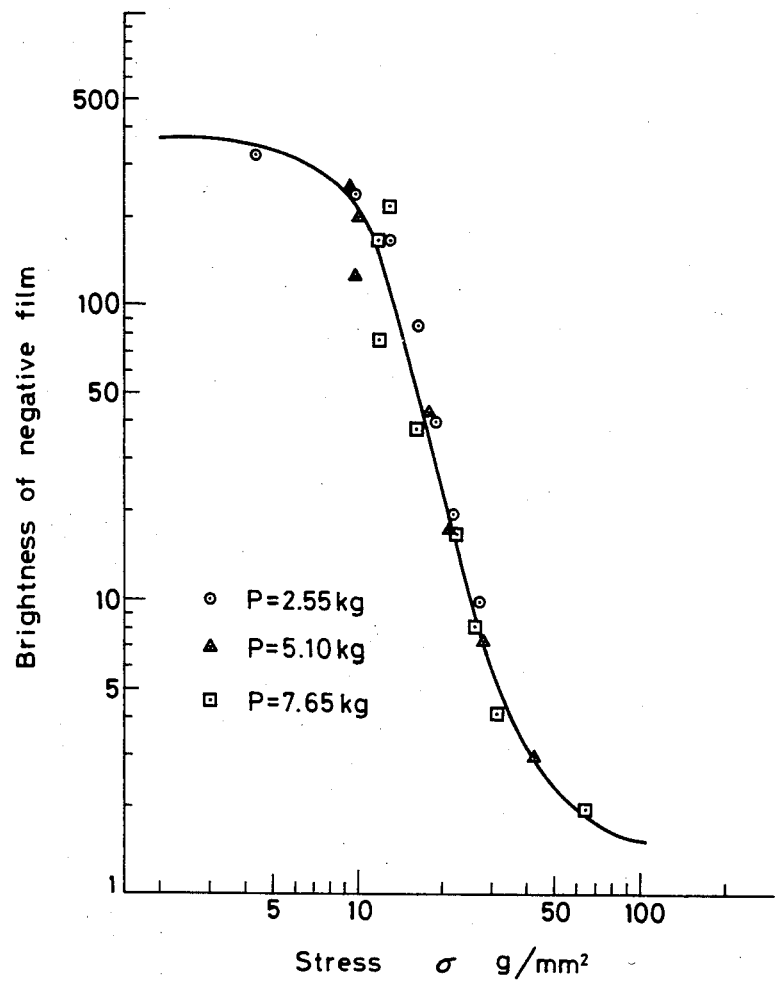
FIG. 5 is a graph of a calibration curve showing the relationship between the brightness of the negative film obtained from the synthesized picture and the stress.

On the other hand, a calibration curve between the brightness of image and the stress value as shown in FIG. 5 was obtained by providing the synthesized picture by applying a concentrated load to the glass test piece by using the apparatus that is shown in FIG. 4. The brightness corresponds to the output voltage of the brightness distribution measuring apparatus.

Figure 6:
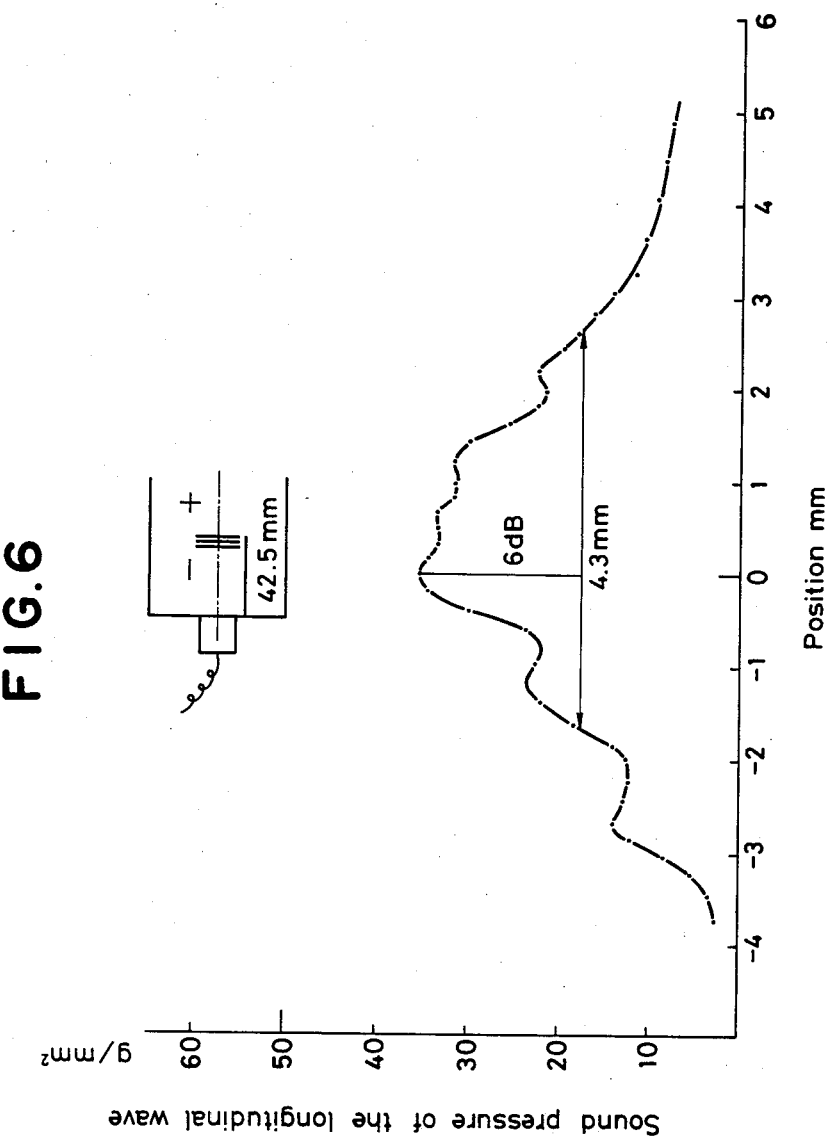
FIGS. 6 to 9 are graphs of the sound pressure distribution of the probe obtained by the method of the present invention.
Figure 7:
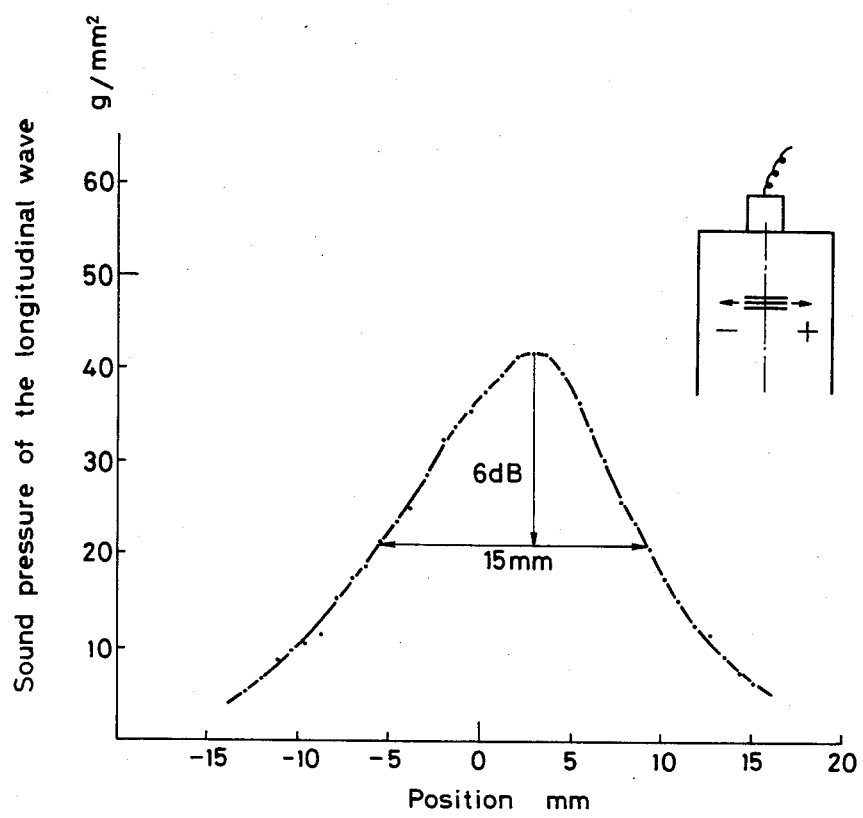
Figure 8:
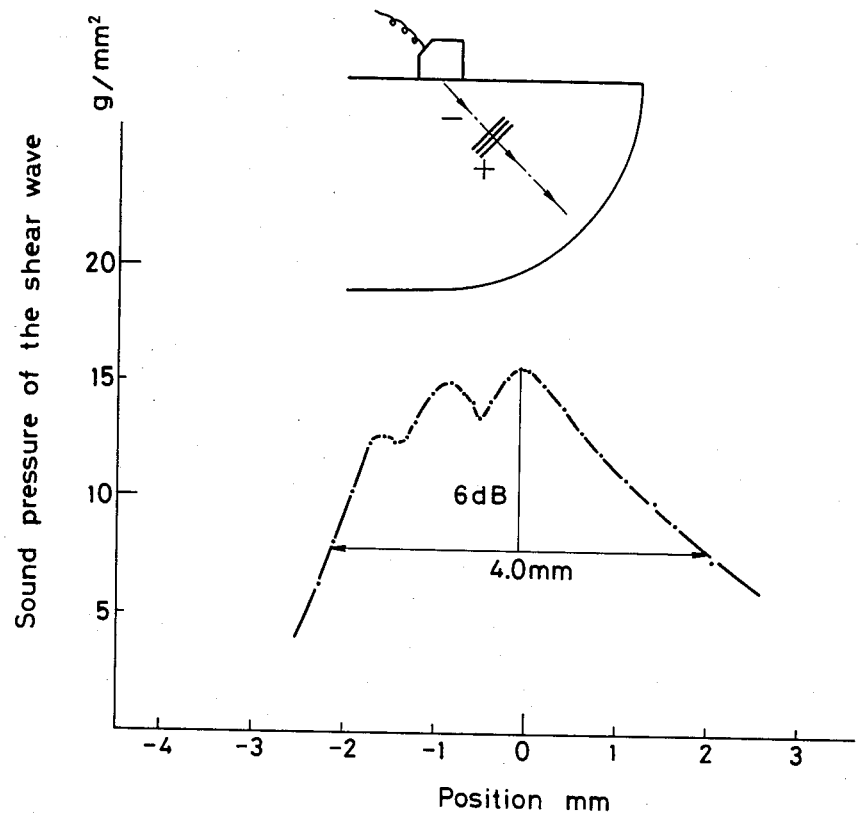
Figure 9:
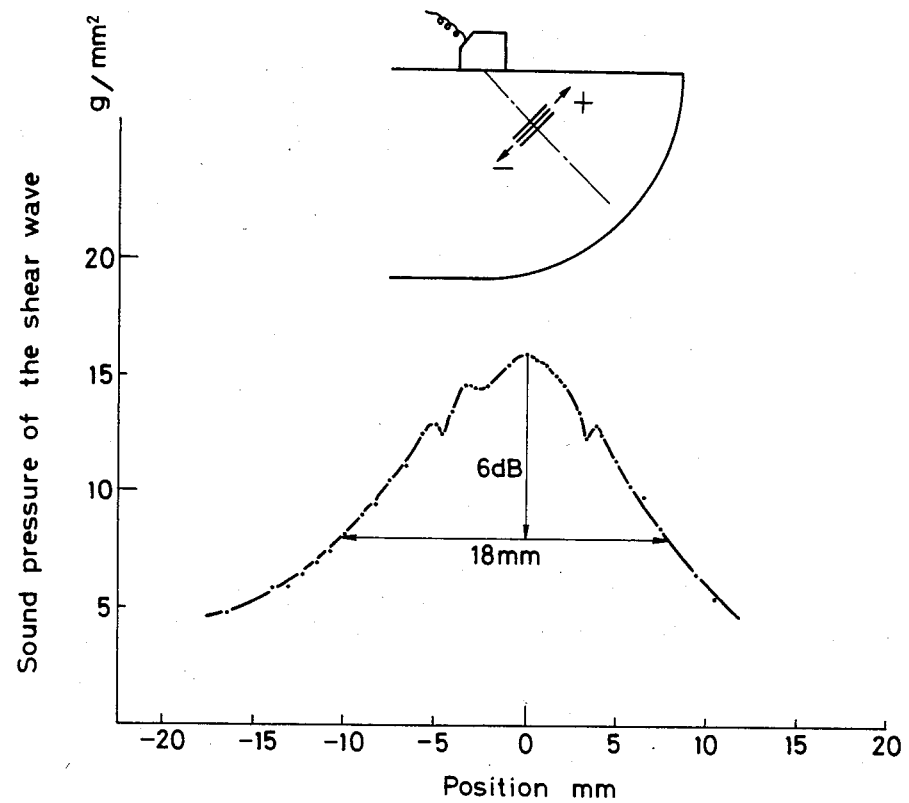

FIGS. 6 to 9 show sound pressure distributions. The sound distribution of FIGS. 6 to 9 are obtained in such a manner that the brightness distribution of the longitudinal and shear waves shown in FIGS. 10 and 11 respectively are measured on the basis of the calibration curve in FIG. 5, and the brightness distributions are converted to the sound pressure distributions. FIG. 6 shows a sound pressure distribution on the center line of the normal longitudinal wave probe; FIG. 7 shows a sound pressure distribution in the transversal direction; FIG. 8 shows a sound pressure distribution in the transmission direction of the angle shear wave probe; and FIG. 9 shows a sound pressure distribution in the transversal direction.

As is apparent from FIGS. 10–13, according to the present invention, the sound pressure distribution of the pulse generated from the probe can be measured and the characteristics of the probe can be evaluated and defined.

As mentioned before, the object of the present invention is to develop a method having a sensitivity which is higher than that of the conventional method using the circular polarization of photoelasticity. It has been known that the object of the present invention can be achieved by synthesizing two pictures, in which the direction of the principal axis is different by 45°, and using a linear polariscope, as shown in FIGS. 10 and 11. It is apparent that the visual images shown by the FIGS. 10 and 11 are much clearer than the conventional images shown by FIGS. 12 and 13. According to the present invention, it has been possible to measure the sound pressure quantitatively.

Furthermore, the visual images shown in FIGS. 10 and 11 show the pulse waveform emitted from the probe, the travelling direction, and existence of extraneous pulse data. From the sound pressure distribution on the waveform as shown in FIGS. 6 to 9, it is possible to evaluate and define the characteristics of the probe, such as the maximum value and its position of the sound pressure, the width of the pulse concerning a resolution (for example the width at the level at 6 db), and directivity characteristics.

The measurement of the brightness distribution is effected by enlarging the negative film and moving a phototransistor by using an X-Y stage, and then the sound pressure value is obtained. However, by using an image processing apparatus, the sequential process from the image synthesization to the evaluation is performed by using a computer thereby to obtain speedy processing.

Referring to Table 1, advantages of the present method over the conventional method are shown.

TABLE 1

Comparison between the present method and the conventional method

| | Method using a standard test piece | Method using an electro-dynamic sensor | Method using visual images | |
|---|---|---|---|---|
| | | | Conventional method | Present method |
| Evaluation of the characteristics of probe | | | | |
| Pulse waveform | Difficult | Difficult | Partially possible | Possible |
| Sound pressure distribution | Relative distribution | Relative distribution | Difficult | Possible |
| Sensitivity of transmitting and receiving the pulse | Difficult | Difficult | Difficult | All is possible since the evaluation is effected on the basis of the pulse waveform and the sound pressure distribution. It is possible to evaluate quantitatively. |
| Resolution | Possible | Partially possible | Partially possible | |
| Distance-amplitude characteristics | Possible | Possible | Difficult | |
| Development of new type probe | May be of reference | May be of reference | May be of reference | |
| Application to flaw detection | | | | |
| Selection of most suitable probe | Partially possible | Partially possible | Partially may be of reference | All is possible, if the model having the same formation as the object is provided. |
| Determination of scanning pitch | Possible | Possible | Partially may be of reference | |
| Arrangement of probes to the object having complex formation. | Difficult | Difficult | Possible | |
| Evaluation of flaw detection results | Difficult | Difficult | Partially possible | |

What is claimed is:
1. A method for determining a sound pressure distribution in a solid body, comprising:
launching into the solid body an ultrasonic pulse waveform;
directing light from a stroboscopic light source into the solid body during a time when the pulse waveform is propagating in the solid body, through a linear polarization device having a principal axis which is aligned at a first predetermined angle;

generating a first image of the light passing through the body with the principal axis at the first predetermined angle;

generating a second image of the light passing through the solid body with the principal axis offset at about 45° from the predetermined first angle; and combining the first and second images to produce a synthesized image.

2. The method of claim 1, wherein said pulse waveform is launched from a probe and further comprising the step of evaluating and defining the characteristics of the probe by analyzing the synthesized image.

3. A method as in claim 1, further comprising the step of analyzing the synthesized image and determining therefrom a relationship between the propagation of the ultrasonic pulse waveform in the solid body and the sound pressure distribution in the solid body relative to the propagating ultrasonic pulse waveform.

4. A method as in claim 3, further including generating a calibration curve which relates the brightness of the light to a stress in the solid body, the calibration curve being obtained by subjecting the solid body to a plurality of known stress values and measuring the brightness of the light in the solid body for each of the known stress values, and wherein the step of determining the sound pressure distribution in the solid body includes determining the brightness of the synthesized image at a plurality of predetermined points thereon and converting the brightness to stress values at each of the predetermined points by reference to the calibration curve.

5. A method as in claim 1, comprising directing the light from the light source into the solid body a predetermined time after launching the ultrasound pulse waveform thereinto.

6. A method as in claim 1, comprising generating the first and second images with a 35 mm. camera.

7. A method as in claim 1, in which a first brightness is associated with the first image and a second brightness is associated with the second image and wherein the step of combining the first and second images includes combining the values of the first and second brightness at predetermined points on the first and second images to generate therefrom the synthesized image.

8. A method as in claim 1, in which a first brightness is associated with the first image and the first brightness is defined by the equation:

$$I_1 = a^2 \cdot \sin^2 2\theta \cdot \sin^2 \delta/2 \ldots$$

and wherein a second brightness is associated with the second image and the second brightness is defined by the equation:

$$I_2 = a^2 \cdot \cos^2 2\theta \cdot \sin^2 \delta/2 \ldots$$

wherein:
$I_1$ is the brightness at predetermined points on the first image;
a is a constant;
$\theta$ is the angle between the principal axis and the principal stress direction of the stress field;
$\delta$ is equal to: $C \cdot d \cdot (\sigma_1 - \sigma_2) \ldots$ and C is a photoelastic constant; d is the thickness of the solid object and $\sigma_1$ and $\sigma_2$ represent principal stresses; and
$I_2$ is the brightness at the predetermined points on the second image;
the synthesized image being formed by combining the first and second brightness at the predetermined points on the synthesized image according to the equation:

$$I = I_1 + I_2 = a^2 \cdot \sin^2 \delta/2 \ldots$$

9. A method as in claim 1, wherein the solid body comprises pyrex glass and including launching the pulse waveform from a probe and evaluating and characterizing the probe for use in testing steel materials.

* * * * *